(12) United States Patent
Ingels

(10) Patent No.: US 8,210,845 B1
(45) Date of Patent: Jul. 3, 2012

(54) ORTHODONTIC PLIERS

(76) Inventor: Luis Ingels, Duarte, CA (US)

(*) Notice: Subject to any disclaimer, the term of this patent is extended or adjusted under 35 U.S.C. 154(b) by 0 days.

(21) Appl. No.: 13/100,696

(22) Filed: May 4, 2011

(51) Int. Cl.
*A61C 3/00* (2006.01)
(52) U.S. Cl. .......................... 433/4; 433/159
(58) Field of Classification Search ............. 433/3, 4, 433/159, 160; 140/106, 121; 81/300–427
See application file for complete search history.

(56) References Cited

U.S. PATENT DOCUMENTS

| | | | | |
|---|---|---|---|---|
| 168,012 A * | 9/1875 | Gaillard et al. | ............... | 433/146 |
| 680,119 A * | 8/1901 | Brewer et al. | ................ | 433/160 |
| 953,170 A * | 3/1910 | Hansen et al. | .................. | 7/134 |
| 1,159,621 A * | 11/1915 | Thomson et al. | ............... | 30/226 |
| 1,475,569 A * | 11/1923 | Dondero | ........................ | 81/416 |
| 1,843,819 A * | 2/1932 | Jackson | ........................ | 81/416 |
| 2,611,288 A * | 9/1952 | Schiffbauer | .................... | 81/416 |
| 2,632,661 A * | 3/1953 | Cristofv | ........................ | 403/119 |
| 3,982,450 A * | 9/1976 | Marsh | ............................ | 81/416 |
| 5,197,879 A * | 3/1993 | Fowler et al. | ................. | 433/159 |
| 5,232,360 A * | 8/1993 | Ingels | .............................. | 433/4 |
| 5,257,558 A * | 11/1993 | Farzin-Nia et al. | ............. | 81/418 |
| 6,000,941 A * | 12/1999 | Ingels | .......................... | 433/159 |
| 6,176,158 B1 * | 1/2001 | Chen | .............................. | 81/417 |
| 7,258,047 B1 * | 8/2007 | Wolter et al. | ................... | 81/416 |
| 7,318,725 B2 * | 1/2008 | Zepf | ............................ | 433/159 |
| 2003/0207234 A1 * | 11/2003 | Brilliant et al. | ............... | 433/159 |
| 2004/0166475 A1 * | 8/2004 | Nikolov | ........................ | 433/159 |
| 2005/0011321 A1 * | 1/2005 | Hsien | ............................ | 81/417 |
| 2005/0186536 A1 * | 8/2005 | Zepf | ............................ | 433/159 |
| 2006/0183076 A1 * | 8/2006 | Nikolov | ........................ | 433/159 |
| 2006/0233622 A1 * | 10/2006 | Bauman | ..................... | 408/239 R |
| 2010/0086889 A1 * | 4/2010 | Lindquist | ........................... | 433/4 |

* cited by examiner

*Primary Examiner* — Cris L Rodriguez
*Assistant Examiner* — Matthew Saunders
(74) *Attorney, Agent, or Firm* — Michael Fedrick; Loza & Loza, LLP

(57) ABSTRACT

A two piece orthodontic pliers having a pair of arms separably hinged together, in which a first hinge portion on a first arm includes a shaft having a central, axially projecting protrusion, and a second hinge portion on a second arm includes a bore having a central recess for receiving the shaft and the central protrusion of the first hinge portion.

16 Claims, 11 Drawing Sheets

ORTHODONTIC PLIERS

BACKGROUND

Orthodontic pliers can comprise two separable parts, each of which has a handle and some type of jaw device. The parts are generally joined by a hinge which must be disassembled to separate the parts. Examples of such separable pliers include those disclosed in U.S. Pat. No. 5,197,879 to Fowler and U.S. Pat. Nos. 5,232,360 and 6,000,941 to Ingels.

The Fowler pliers illustrate the problems involved when utilizing a pinless hinge. The Fowler pliers rely on a dovetail arrangement to hold the pliers parts together over a predetermined extent of opening of the handles and jaws. Beyond that limit, the parts separate from one another, and the pliers fall apart. The relatively short dovetail surfaces also tend to wear due to the squeezing of the handles together.

The Ingels patents provides a hinge that has a pin and a recess which both center the parts and more evenly spread the wear experienced by such parts. The parts are prevented from separating by overhanging shoulders of limited extent, and readily separate when their handles are separated beyond this extent.

SUMMARY

There remains a need for separable pliers, in particular for orthodontic use, in which the separable parts are retained more securely by a hinge portion of the pliers. The pliers of the present invention comprise separable first and a second pliers parts that are retained more securely than the components of prior separable pliers. In the present pliers, each pliers part comprises a handle, a jaw, and a hinge portion between the handle and the jaw, with the hinge portions of each pliers part together forming a hinge. The jaws can be provided with a cutting edge.

The hinge of the first pliers part comprises a pair of arcuate blades while the hinge of the second pliers part comprises a pair of arcuate grooves. Preferably, each of the arcuate grooves is formed with an overhanging shoulder that engages one of the arcuate blades to prevent separation of the first and a second pliers parts when the first and a second pliers parts are engaged to form the pliers. The blades and grooves extend concentrically around a central axis of the hinge and are of limited arcuate length, so that the blades engage the grooves when the handles of the first and second pliers parts are opened to a limited extent and disengage the grooves when the handles of the first and second pliers parts are opened beyond the limited extent, thereby allowing the first and second pliers parts to be separated. The arcuate blades preferably form an intercepted arc of less than 90°, and more preferably one of less than 45°.

One of the hinge portions of the present pliers is a male hinge portion that comprises a projection with a longitudinal axis. The projection has a cylindrical peripheral bearing wall and a distal face, the distal face further comprising a central protrusion extending axially therefrom. The central protrusion can have side walls that are cylindrical or rounded (convex), and the distal face of the central protrusion can be flat or rounded. Preferably, a spring ring is positioned around the projection of the male hinge portion.

The other hinge portion is a female hinge portion that comprises a bore having a peripheral bearing wall for receiving the projection of the male hinge portion. The bearing walls of the female hinge portion are close fitting and concentric, with the bore comprising a proximal face having a recess for receiving the central protrusion of the male hinge portion when the first and second pliers parts are engaged to form the pliers. The recess can, in one embodiment, further include an insert having an upper face for engaging the distal face of the central protrusion of the male hinge portion. The insert can be retained in the recess by threaded engagement, thereby allowing the distance between the distal face of the insert and a lower surface of the recess to be adjusted by rotating the insert. The insert can, for example, comprise a cylindrical nut with peripheral threads for engaging mating grooves in the side walls of the recess and a central hexagonal opening for receiving a mating portion of a hexagonal wrench.

In a further embodiment, the present pliers can further include a lip on one of the handles, the lip facing the other handle; a spring arm on the other handle, the spring arm facing the lip and extending toward the hinge; and a hook on the spring arm disposed to engage the lip and prevent further separation of the handles until the spring arm is bent to release the hook from the lip. The lip and spring arm in this embodiment are preferably integrally formed with their respective handles. The spring arm is also preferably blade-like, and in which case the hook can comprise a curved tip to engage the lip.

FIGURES

Figure 14:
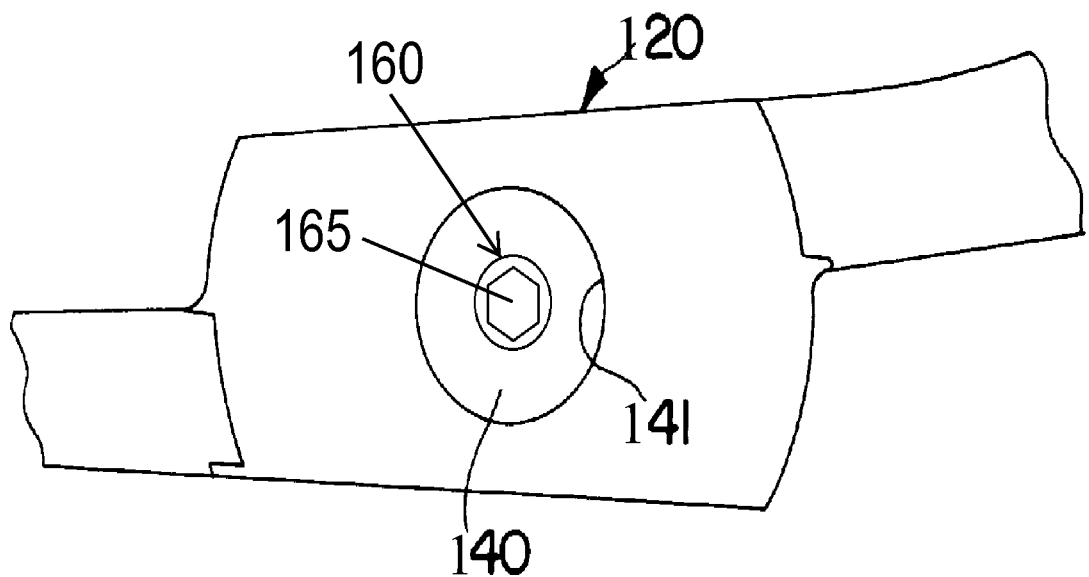

FIG. 14 a fragmentary plan view of another embodiment of the other component of the pliers of claim 8.

Figure 13:
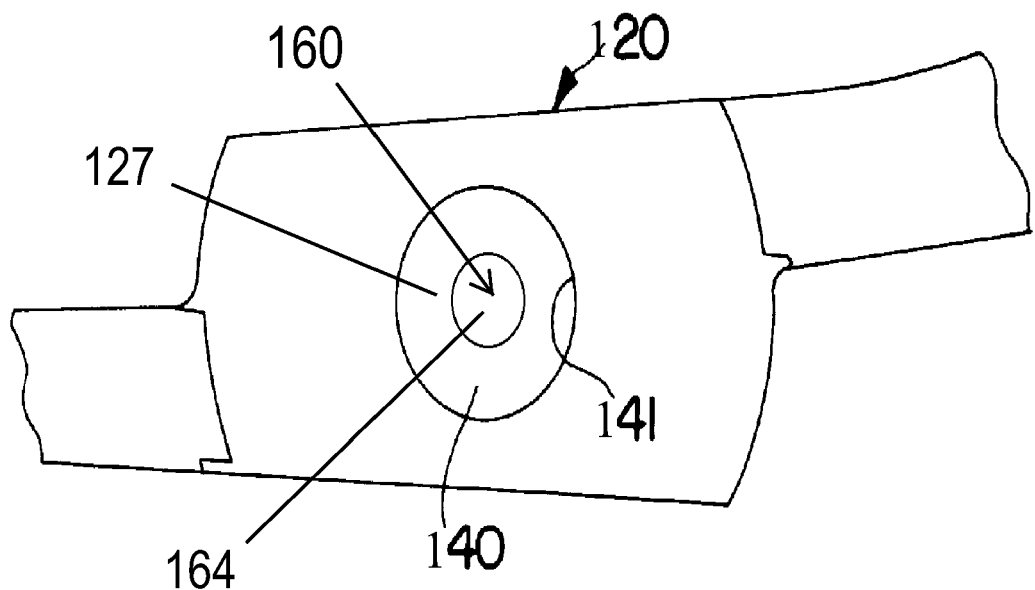
FIG. 13 is a fragmentary plan view of an embodiment of the other component of the pliers of claim 8.
Figure 15:
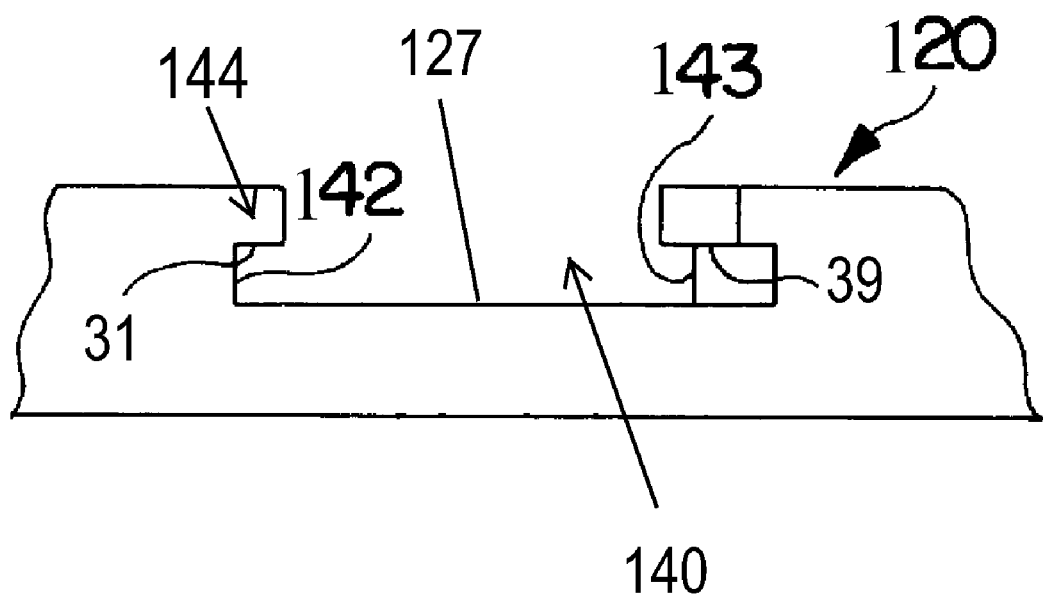

FIG. 15 is a side view of the component of FIG. 13.

DESCRIPTION

Definitions

As used herein, the following terms and variations thereof have the meanings given below, unless a different meaning is clearly intended by the context in which such term is used.

"Arc" refers to a portion of a circle between two points on the circle. An intercepted arc refers to an arc intercepted by an angle, i.e. in which each endpoint of the arc is on a different ray of the angle.

"Blade" refers to a broad, flat component. The blades described herein generally comprise a blunt edge.

"Hinge" refers to a joint that holds two parts together so that one part can articulate and move relative to the other.

"Jaws" refer to the opposable flange portions of a pair of pliers, with a "jaw" referring to a single jaw member.

"Pliers" refers to a hand tool having two hinged arms and a pair of pivoted, opposing jaw members used for holding, bending, or cutting. A "pair of pliers" denotes a single pliers instrument, while "pliers" can denote one or more than one instrument.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Pliers

Figure 1:
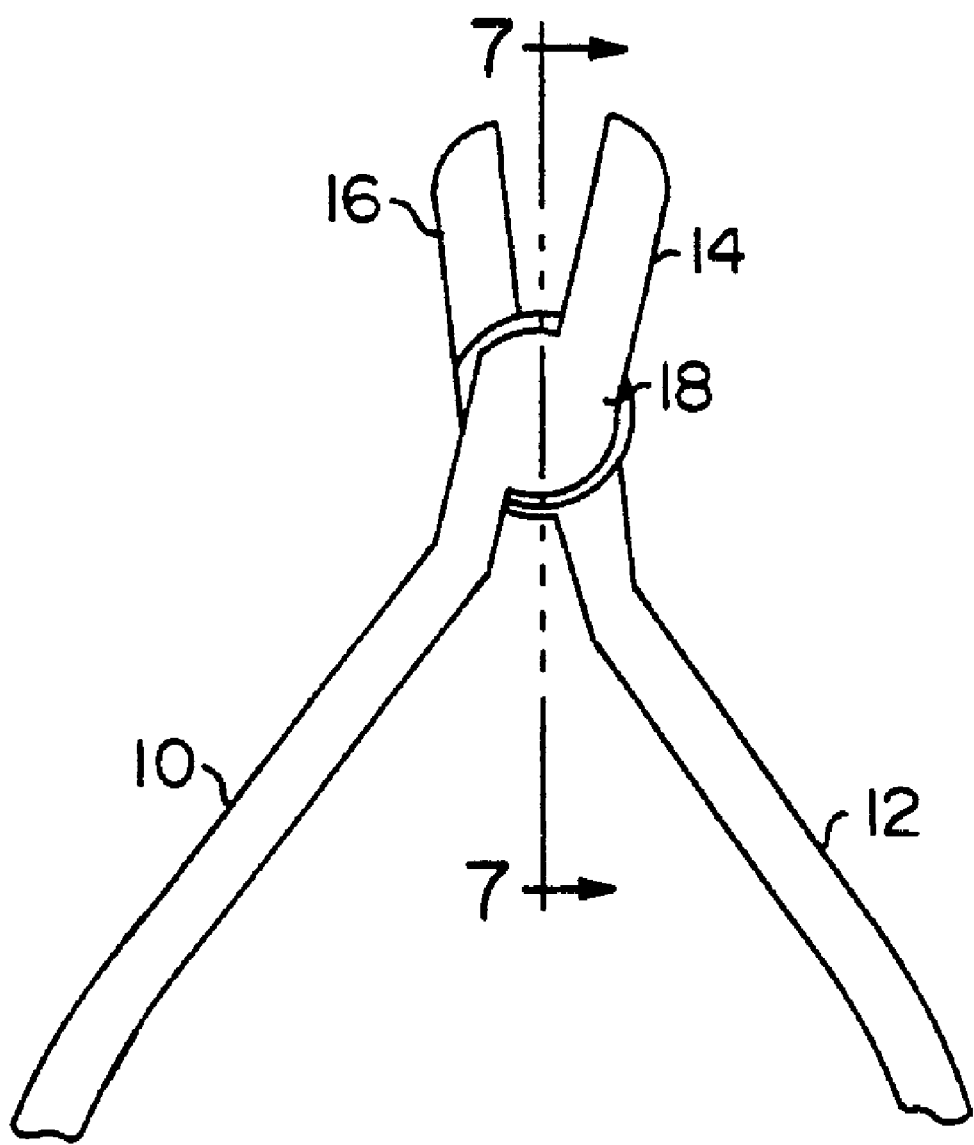
FIG. 1 is a plan view of an embodiment of pliers of the invention.
Figure 2:
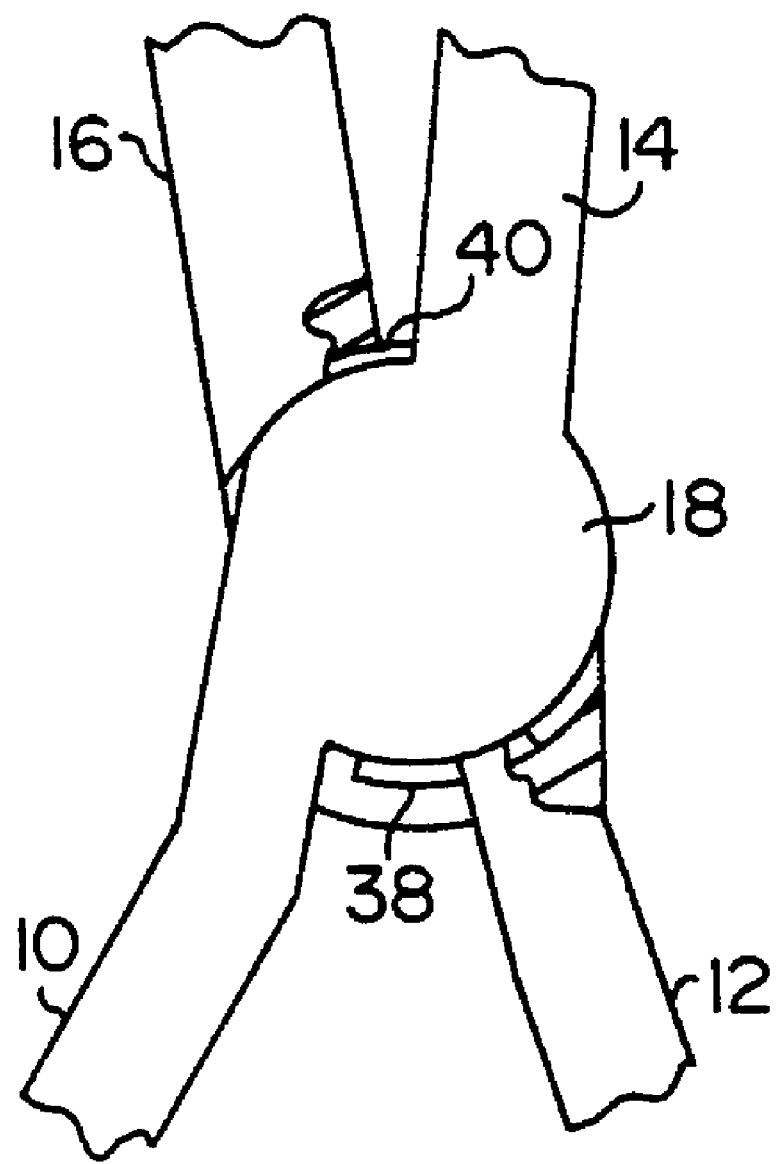
FIG. 2 is a plan view, partially in cutaway cross-section, of the pliers of FIG. 1.

An embodiment of the present invention is shown in FIG. 1. In this embodiment, a protruding shaft (projection) on the swivel axis of one handle engages a bore on the matching swivel axis of the other pliers handle, and a resilient spring ring is preferably provided on the shaft to aid in retention of the shaft in the bore. Channels in the body of the handle containing the bore are provided to receive and contain arcuate segments of protruding ribs or blades on the other handle around the axis of rotation of the swivel joint (hinge) connecting the plier handles. Disengaging the blades from the channels by opening the pliers to a predetermined extent permits withdrawal of the shaft from the bore for disassembly.

Figure 7:
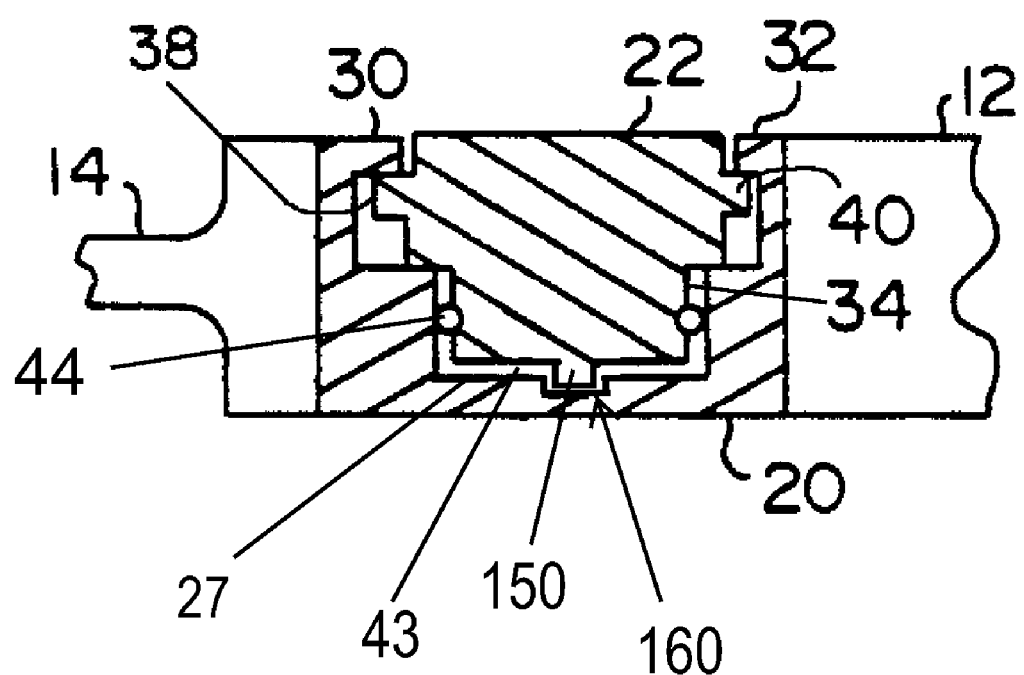
FIG. 7 is a fragmentary cross-section taken on line 7-7 of FIG. 1.

In this embodiment, a swivel assembly joins the two handle members 10 and 12. Jaw members 14 and 16 are connected integrally to the handle members 10 and 12 respectively by the swivel assembly 18. Each handle member has a reduced swivel section which combines with the other to form the total thickness of the tool which can be seen in FIG. 7 as receiving swivel section 20 belonging to handle member 12, and projecting swivel section 22 which is part of handle member 10.

Figure 3:
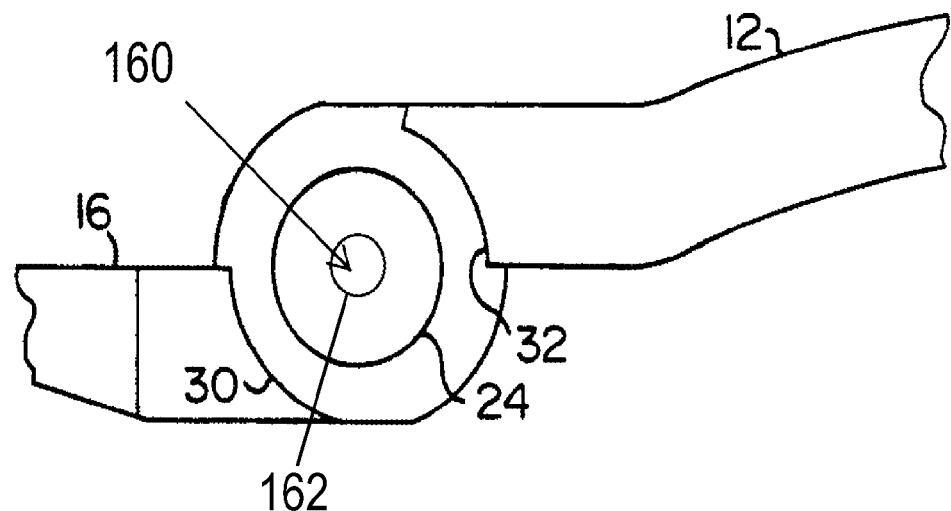
FIG. 3 is a plan view of a fragment of a first disassembled handle of the pliers of FIG. 1.
Figure 4:
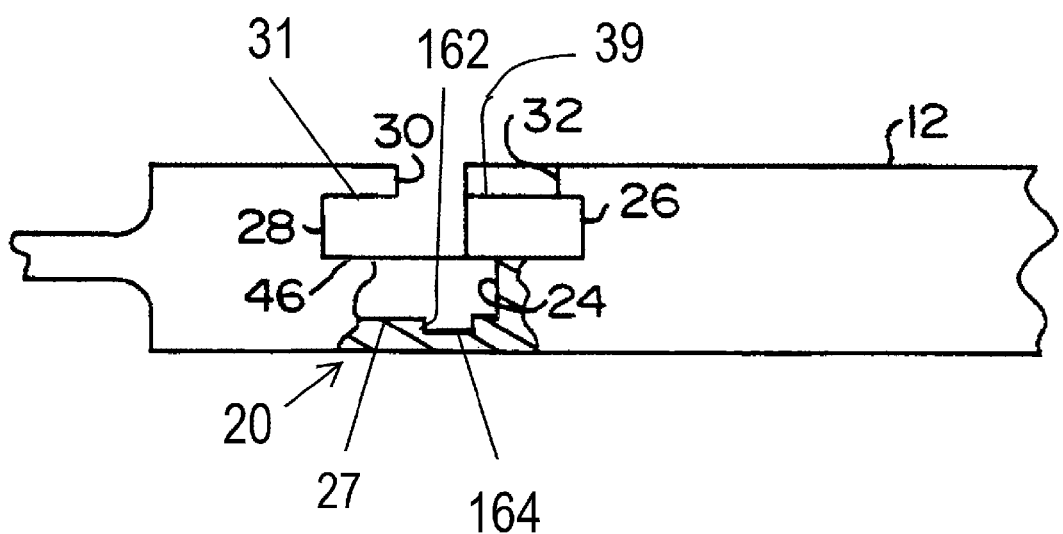
FIG. 4 is a fragmentary side elevation, partially in cross-section, of the handle shown in FIG. 3.

As can be seen in FIGS. 3 and 4, handle member 12 has a receiving center swivel section 20 which has a bore 24 partially therethrough and under-cut channels 26 and 28 which are segments of cylindrical walls coaxial with bore 24, which comprise inwardly projecting rims or flanges 30 and 32 that are preferably the same length as channel segments 26 and 28 and coaxial with bore 24, and are diametrically opposed. Channels 26 and 28 form a flat shoulder 46 which defines the thickness of the swivel 20.

The bore 24 further includes a proximal (upper) face 27. Proximal face 27 is shaped to conform to a distal face 43 of a cylindrical shaft 34 in the projecting swivel section 22 so as to allow the two surfaces to articulate with respect to each other during the opening and closing of the present pliers. In a preferred embodiment, both the proximal face 27 and distal face 43 are substantially planar, though other shapes are possible. For example, proximal face 27 can be concave and distal face 43 can be correspondingly convex.

In a central portion of proximal face 27 of receiving swivel section 20, the proximal face 27 further comprises a recess 160 for receiving a central protrusion 150 located on in a central portion of the distal face 43 of projecting swivel section 22. The recess 160 comprises side wall 162 and proximal (upper) face 164. The side wall 162 is preferably cylindrical, and the proximal face 164 is preferably substantially planar, like proximal face 27 of receiving swivel section 20, although it can also be concave or convex. The side wall 162 and proximal face 164 of the recess 160 are preferably shaped to correspond to the shape of the side wall 152 and distal face 154 of the central protrusion 150.

Figure 5:
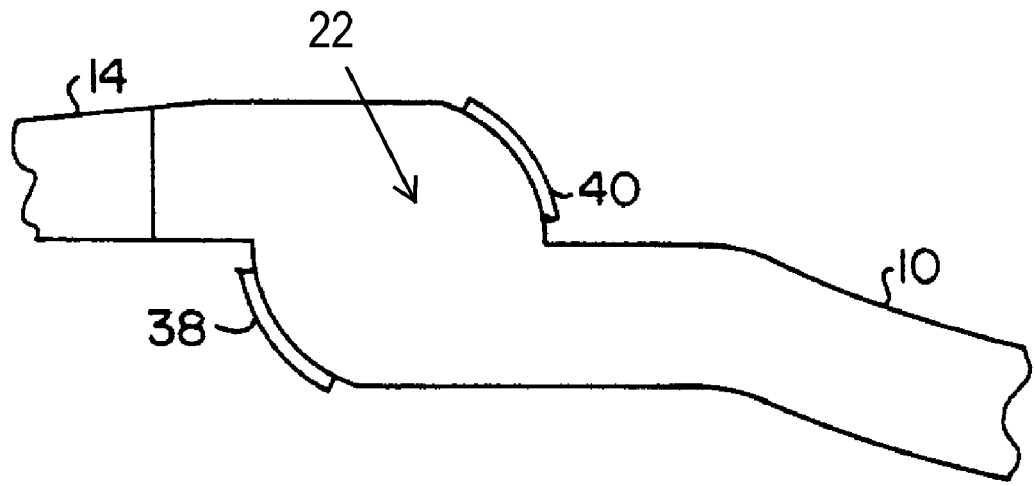
FIG. 5 is a plan view of a fragment of the second disassembled handle of the embodiment of FIG. 1.
Figure 6:
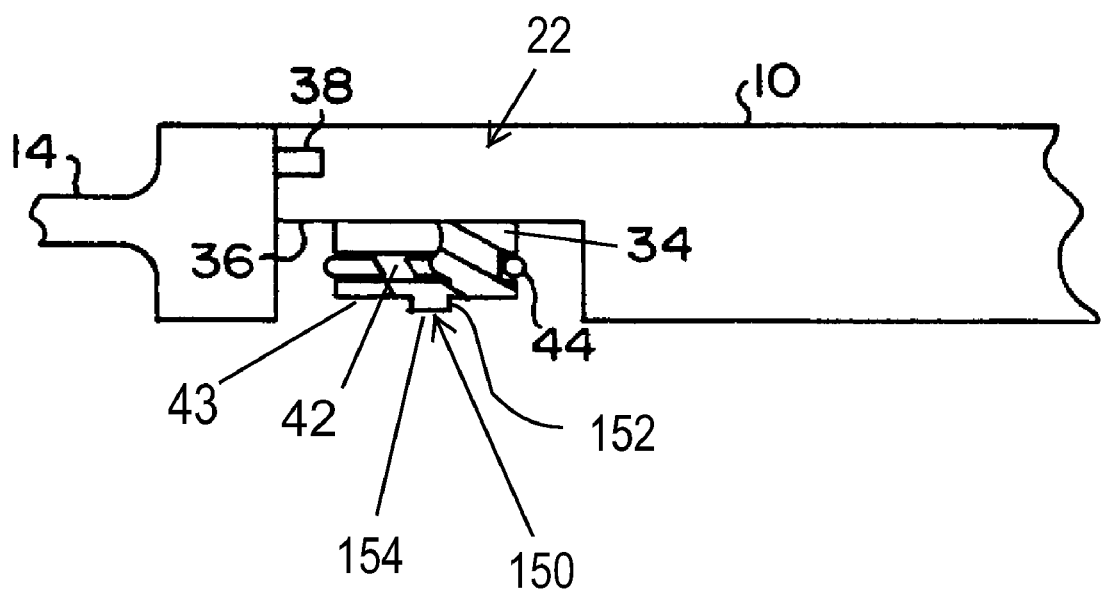
FIG. 6 is a fragmentary side elevation, partially in cross-section, of the second disassembled handle shown in FIG. 5.

In FIGS. 5 and 6, handle member 10 is shown with its projecting swivel section 22 which has a cylindrical shaft 34 protruding from a counterbore face 36. Shaft 34 rotates around the axis of rotation of handle member 10. Protruding blades 38 and 40 are segments of tubular cylinders radially opposed but coaxial with shaft 34. Shaft 34 preferably has a peripheral annular groove 42 and a split spring ring 44 installed therein.

Distal face 43 of the cylindrical shaft 34 of projecting swivel section 22 of the present pliers further comprises the central protrusion 150, which extends axially away from the distal face 43, i.e. toward proximal faces 27 and 164 of the receiving swivel section 20 when the pliers parts are connected for use. When joined, the distal face 154 of the central protrusion 150 of projecting swivel section 22 contacts the proximal face 164 of the recess 160, and the side walls 152 of central protrusion 150 fit within the recess 160. Through the use of the central protrusion 150, a tighter interference fit between the pliers parts, in particular between the receiving swivel section 20 and the projecting swivel section 22, is created. Specifically, use of the central protrusion 150 results in a closer fit between the lower surface 31 of inwardly projecting rim 30 and the upper surface of protruding blade 38, and between the lower surface 39 of inwardly projecting rim 32 and the upper surface of protruding blade 40.

The recess 160 can, in one embodiment, further include an insert 165 (shown in FIG. 14) having an upper face for engaging the distal face 154 of the central protrusion 150 of the projecting swivel section 22. The insert 165 can be retained in the recess 160 by threaded engagement, thereby allowing the distance between the upper face of the insert and a lower surface of the recess (i.e., proximal face 164) to be adjusted by rotating the insert 165. In this embodiment, the insert can, for example, comprise a cylindrical nut with peripheral threads for engaging mating grooves in the side walls of the recess and a central hexagonal opening for receiving a mating portion of a hexagonal wrench, as shown in FIG. 14, thought other tool engagement portions can also be used, such as for a flat head or Phillips head screwdriver. Alternatively, the insert 165 can be fixedly placed within the recess 160 in order to adjust the tightness of the fit between the two pliers portions of the present pliers.

In the process of assembling the pliers after cleaning, the handles are held in their open position. Shaft 34 of handle 10 is pushed into bore 24 of handle 12 against the spring resistance of spring ring 44 (if present), and the central protrusion 150 is fitted into the recess 160. In the most open position of handle members 10 and 12, the blades 38 and 40 are free of engagement with rims 30 and 32 of handle 12. When counter bore face 34 meets shoulder 46 of handle 12, the handles 10 and 12 can be rotated toward each other to engage the protruding blades 38 and 40 with the rims 30 and 32 of the channels 26 and 28, thereby holding the device in assembly for use. The working rotation of the instrument is essentially the length of engagement in rotation of the blades 38 and 40 with the channels 26 and 28. Disassembly for cleaning and sterilization is the reverse of the above described process.

Another embodiment of the present invention is shown in FIGS. 8-15. A separable orthodontic pliers according to this embodiment, as in the embodiment described above, includes a first pliers part and a second pliers part. Each part includes a handle, a jaw member, and a hinge portion between them. The hinge portion on one part comprises a cylindrical shaft having a peripheral bearing wall, while the hinge portion of the other part comprises a bore with a peripheral bearing wall.

The bearing walls have substantially the same diameter so as to make a close rotational fit with one another.

One of the pliers parts in this embodiment includes a projection or lip 115 spaced from its handle and facing toward its hinge portion. The other pliers part includes an integral flexible spring arm 123, extending away from it toward the lip 115. The spring arm 123 has at its free end a hook 124 disposed and arranged to engage the lip 115 when the handles are at their maximum permissible spacing apart without risk of separation. The spring arm 123 is formed so as to bear against the lip 115 to bias the handles apart. Separation is enabled by deflecting the spring arm 123 so its hook 124 passes the lip 115 and the overhangs no longer interfere with the separation of the parts.

Figure 8:
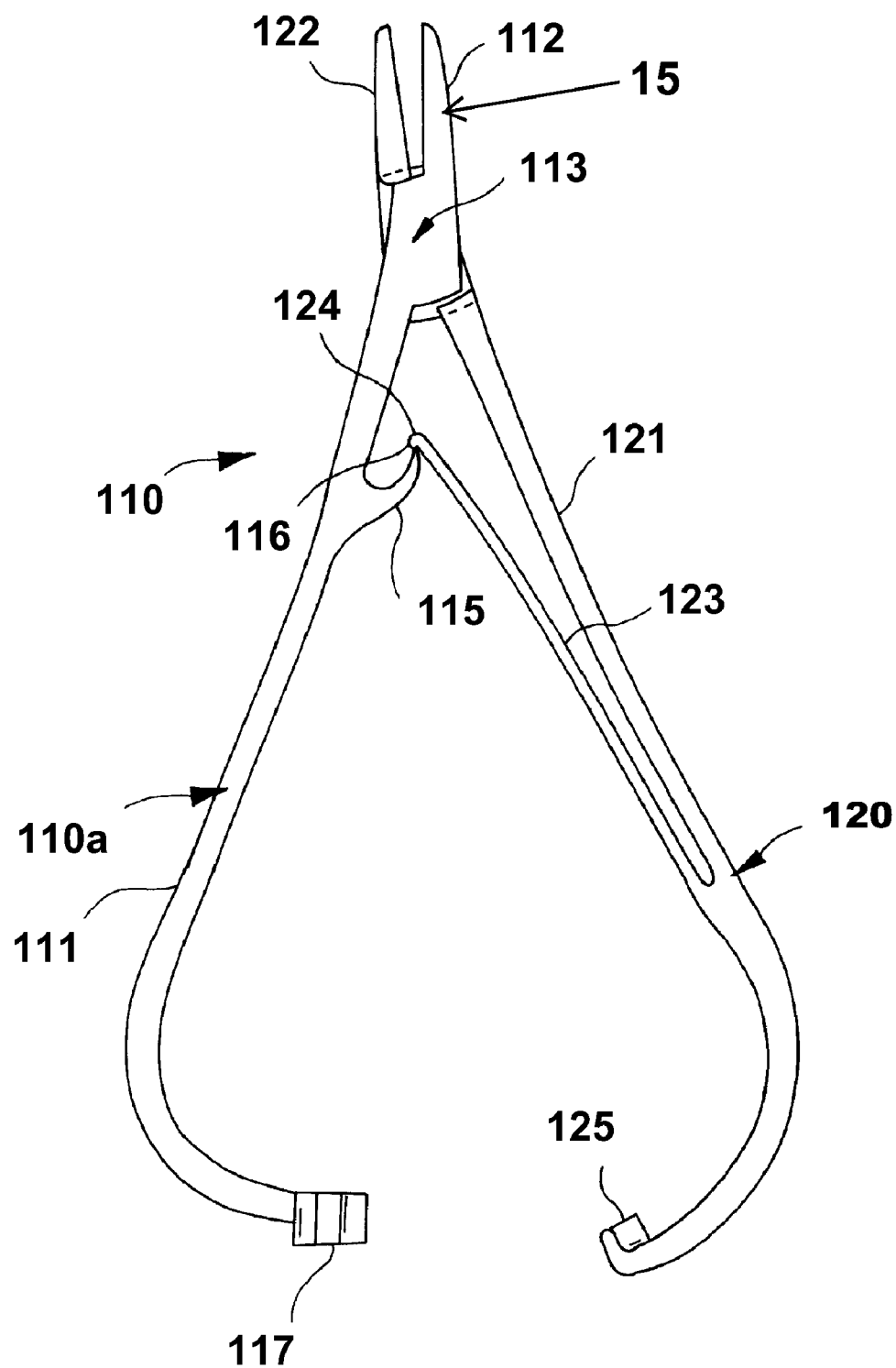
FIG. 8 is a plan view of another embodiment of the present pliers, in a configuration ready for use.

FIG. 8 shows a separable orthodontic pliers 110 of this embodiment in its repose condition, i.e. the maximum opening of the jaws 15 which is permitted without releasing the latch mechanism formed by lip 115 and hook 124. The pliers in this position cannot be reversibly separated, as the plier members 110a, 120 are restrained from opening to an extent that would allow them to be separated without damaging the pliers. First part 110a has a handle 111 and a jaw 112 on opposite sides of a hinge 113. It further includes a lip 115 formed as an integral extension of the handle. The lip has a tip 116 that is spaced from the handle. At its free end a group of ratchet notches 117 are formed for a purpose to be disclosed.

Second part 120 has a handle 121 and a jaw 122 on opposite sides of hinge 113. It further includes an integral spring arm 123 that extends from the handle in the direction of the hinge. The spring arm 123 is a somewhat flexible spring, although it preferably resists bending so as to avoid opening the pliers to an extent that would allow the pliers parts to be disengaged from one another. At its end, the spring arm 123 preferably forms a hook 124 which in the position of FIG. 8 engages the lip 115 and prevents further pivoting apart of the handles unless this engagement is released. The free end of the spring arm 123 preferably includes a ratchet tooth 125 which can releasably engage the tip of lip 115 in ratchet notches 117 in order to hold the handles in an adjustably closed position relative to one another. It is to be understood that the hook could alternatively be retained by the lip 115 rather than by the spring arm 123.

The details of the hinge of this embodiment are shown in FIGS. 11-14. First pliers part 110a (FIG. 11) includes a shaft 130 with a cylindrical peripheral bearing surface 131 having a diameter. It extends from a flat surface 132 which has at its edge two arcuate blades 133, 134 having top and bottom surfaces 135, 136. The blades are centered on the hinge center 137. The shaft 130 includes a distal face 138, and extending axially away from a central portion of the distal face 138 is a central protrusion 150 as described in the previous embodiment of the present pliers.

Second pliers part 120 (FIG. 13) has a bore 140 having a peripheral cylindrical bearing surface 141 with a diameter. The diameters of the bearing surfaces are substantially equal, permitting a close rotational fit which takes most of the wear when the handles are squeezed together. A pair of undercut grooves 142, 143 are formed, each centered on the hinge axis. Each has an overhanging ledge or rim 144. These have about the same arcuate extent as the blades. The grooves have about the same thickness as the blades (though sufficiently larger to allow the blades to fit therein) so as to hold the handles in precise alignment. A central portion of proximal face 127 of the bore 140 comprises a recess 160 as described above for receiving the central protrusion 150 located in a central portion of the distal face 138 of the shaft 130.

It can be seen that with the handles spread apart and the hook and lip disengaged, the parts can be pressed together, inserting the shaft 130 into the bore. Then, rotating the handles, moving them toward each other, the blades enter the grooves and the parts are held together. When joined, the distal face 154 of the central protrusion 150 of the first (male) pliers part contacts the proximal face 164 of the recess 160 (or the upper surface of an insert 165, if present), and the side walls 152 of central protrusion 150 fit within the recess 160. Through the use of the central protrusion 150, a tighter interference fit between the pliers parts is created. Specifically, use of the central protrusion 150 results in a better fit between the lower surfaces 31 and 39 of the inwardly projecting rims 144 of the first (female) pliers part (FIG. 15) and the upper surfaces of protruding blades 133 and 134.

Figure 9:
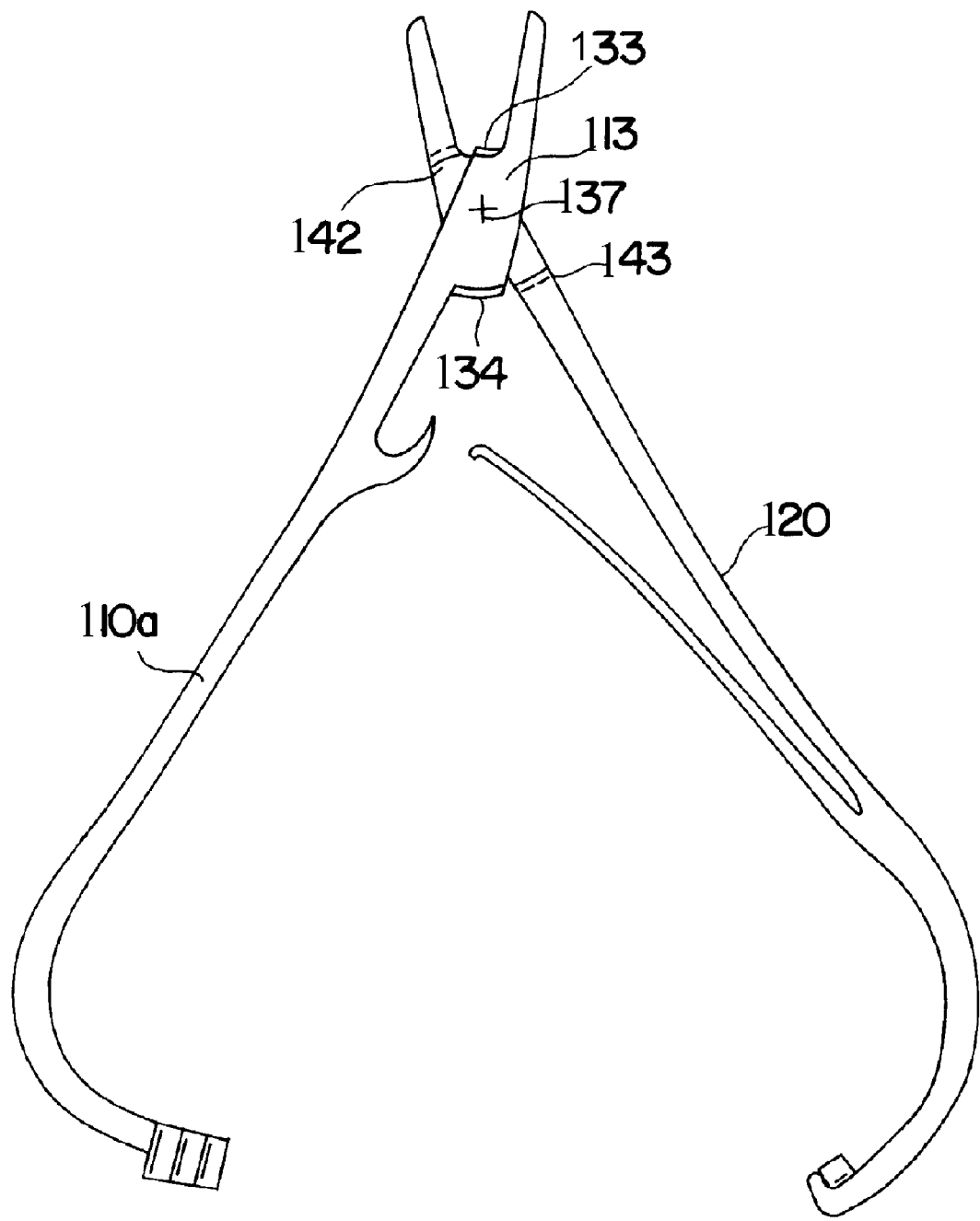
FIG. 9 is a plan view of the pliers of FIG. 8 in a configuration allowing assembly or disassembly of the pliers.
Figure 10:
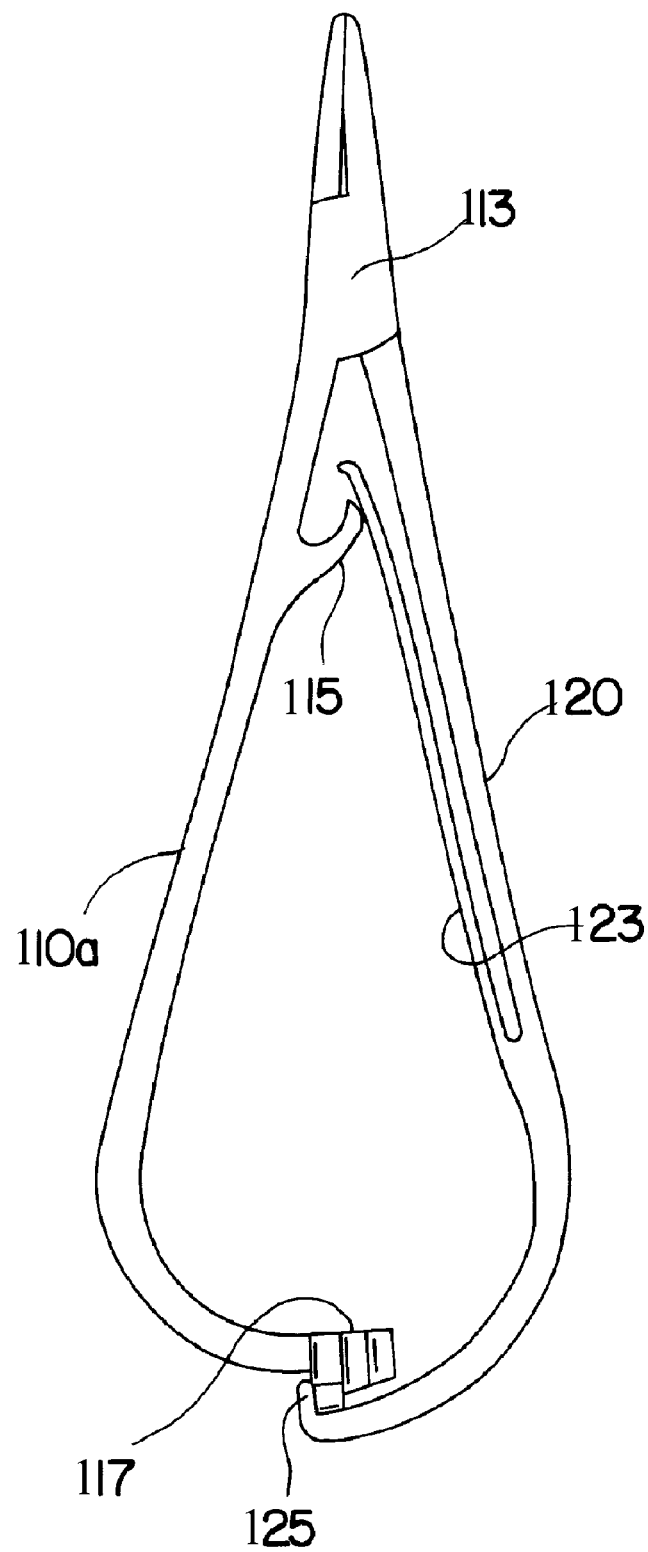
FIG. 10 is a plan view of the pliers of FIG. 8 in a closed and latched configuration.
Figure 11:
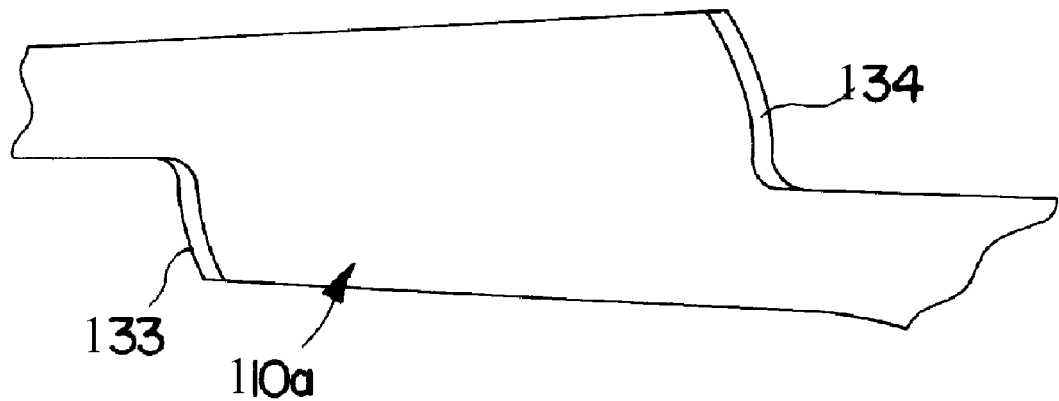
FIG. 11 is a fragmentary plan view of one component of the pliers of claim 8.
Figure 12:
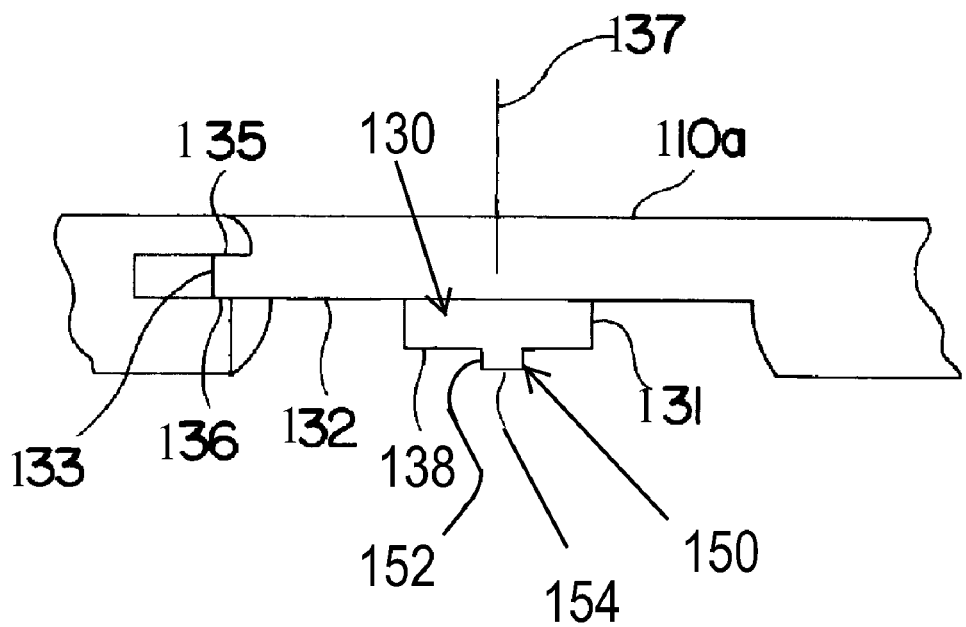
FIG. 12 is a side view of the component of FIG. 11.

The use of this embodiment of the present pliers is shown in FIGS. 8-10. FIG. 8 shows the pliers in the unlatched, fully assembled condition, ready for use. The spring arm 123 has biased the handles apart to the maximum extent permitted without bending (deflecting) the spring arm. The hook 124 has engaged the lip 115, which prevents further separation of the handles. This is a continuing bias useful to the user, and which also strengthens the grip of the hook on the lip. In FIG. 8, the blades are still in the grooves to an extent sufficient to prevent separation of the handles.

The handles can be separated by bending the spring arm 123 inwardly to clear the tip 116 of lip 115, permitting separation as shown in FIG. 9. The parts can then be separated by removing the shaft 130 from the bore. The blades clear the grooves in this position. Reassembly of the pliers requires no more than again plugging the shaft into the bore and moving the handles toward one another to engage the blades in the grooves. The hook and lip will be engaged, and the pliers is ready for use.

It is to be understood that the length and shape of the handles and the working jaws of the pliers can be designed to fit the task for which the tool is to be used. It is well known in the art to design jaws as pin or ligature cutters, loop-forming pliers, distal cutters, wire-bending pliers, band removing pliers and numerous other types. In addition, handle lengths, off-sets and separations can be varied for different tasks. The parts of the pliers are also preferably made of a single piece of metal, usually of stainless steel. The shapes shown herein are readily made on conventional machinery, and can effectively be cleaned and sterilized.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. Pliers having handles, jaws, and a hinge, comprising:
   first and a second pliers parts, each pliers part comprising a handle, a jaw, and a hinge portion between the handle and the jaw, wherein the respective hinge portions together form the hinge;
   a pair of arcuate blades on the hinge portion of the first pliers part and a pair of arcuate grooves on the hinge portion of the second pliers part, wherein the blades and grooves extend concentrically around a central axis of the hinge and are of limited arcuate length, the blades thereby engaging the grooves when the handles of the first and second pliers parts are opened to a limited extent and disengaging the grooves when the handles of the first and second pliers parts are opened beyond the limited extent, thereby allowing the first and second pliers parts to be separated;

wherein one of the hinge portions is a male hinge portion that comprises a shaft with a longitudinal axis, the shaft having a cylindrical peripheral bearing wall and a distal face, the distal face of the shaft further comprising a central protrusion extending axially therefrom, the central protrusion having a distal face; and wherein the other hinge portion is a female hinge portion that comprises a bore having a peripheral bearing wall for receiving the shaft of the male hinge portion, the bearing walls being close fitting with the cylindrical peripheral bearing wall of the shaft and concentric, the bore comprising a proximal face having a recess for receiving the central protrusion of the male hinge portion when the first and second pliers parts are engaged to form the pliers wherein the side walls of the central protrusion fit within the recess and the distal face of the central protrusion contacts the proximal face of the recess when the first and second pliers parts are engaged to form the pliers.

2. The pliers of claim 1, wherein the recess comprises an insert having an upper face for engaging the distal face of the central protrusion of the male hinge portion.

3. The pliers of claim 2, wherein the insert is retained in the recess by threaded engagement, thereby allowing the distance between the distal face of the insert and a lower surface of the recess to be adjusted by rotating the insert.

4. The pliers of claim 3, wherein the insert comprises a cylindrical nut with peripheral threads for engaging mating grooves in the recess, the nut further comprising a central hexagonal opening for receiving a mating portion of a hexagonal wrench.

5. The pliers of claim 1, wherein the central protrusion comprises cylindrical side walls.

6. The pliers of claim 1, wherein the central protrusion comprises convex side walls.

7. The pliers of claim 1, wherein the distal face of the central protrusion is flat.

8. The pliers of claim 1, wherein the distal face of the central protrusion is rounded.

9. The pliers of claim 1, further comprising:
- a lip on one of the handles, the lip facing the other handle;
- a spring arm on the other handle, the spring arm facing the lip and extending toward the hinge; and
- a hook on the spring arm disposed to engage the lip and prevent further separation of the handles until the spring arm is bent to release the hook from the lip.

10. The pliers of claim 9, wherein the lip and the spring arm are integrally formed with their respective handles.

11. The pliers of claim 9, wherein the spring arm is blade-like, and wherein the hook comprises a curved tip to engage the lip.

12. The pliers of claim 1, wherein each of the arcuate grooves is formed with an overhanging shoulder that engages one of the arcuate blades to prevent separation of the first and a second pliers parts when the first and a second pliers parts are engaged to form the pliers.

13. The pliers of claim 1, wherein the arcuate blades form an intercepted arc of less than 90°.

14. The pliers of claim 1, wherein the arcuate blades form an intercepted arc of less than 45°.

15. The pliers of claim 1, further comprising a spring ring positioned around the projection of the male hinge portion.

16. The pliers of claim 1, wherein the jaws are provided with a cutting edge.

* * * * *